US012594322B2

(12) United States Patent
Kim et al.

(10) Patent No.: US 12,594,322 B2
(45) Date of Patent: *Apr. 7, 2026

(54) LIQUID COMPOSITION COMPRISING PROTEIN

(71) Applicant: SAMSUNG BIOEPIS CO., LTD., Incheon (KR)

(72) Inventors: Inae Kim, Seoul (KR); Soyun Jung, Incheon (KR); Jaemin Lee, Seoul (KR); Hun Joo Lee, Incheon (KR); Yongkook Kim, Incheon (KR)

(73) Assignee: SAMSUNG BIOEPIS CO., LTD., Incheon (KR)

( * ) Notice: Subject to any disclaimer, the term of this patent is extended or adjusted under 35 U.S.C. 154(b) by 1021 days.

This patent is subject to a terminal disclaimer.

(21) Appl. No.: 17/274,834

(22) PCT Filed: Sep. 10, 2019

(86) PCT No.: PCT/KR2019/011762
§ 371 (c)(1),
(2) Date: Mar. 10, 2021

(87) PCT Pub. No.: WO2020/055123
PCT Pub. Date: Mar. 19, 2020

(65) Prior Publication Data
US 2022/0054586 A1     Feb. 24, 2022

(30) Foreign Application Priority Data
Sep. 10, 2018     (KR) ........................ 10-2018-0107588

(51) Int. Cl.
*A61K 38/17*     (2006.01)
*A61K 9/00*     (2006.01)
*A61K 47/26*     (2006.01)
(52) U.S. Cl.
CPC .......... *A61K 38/179* (2013.01); *A61K 9/0019* (2013.01); *A61K 9/0048* (2013.01); *A61K 47/26* (2013.01)
(58) Field of Classification Search
CPC ........... A61K 47/26; A61K 47/10; A61K 9/08
See application file for complete search history.

(56) References Cited

U.S. PATENT DOCUMENTS

| | | | |
|---|---|---|---|
| 9,982,032 B2 | 5/2018 | Park et al. | |
| 10,646,546 B2 | 5/2020 | Im et al. | |
| 2019/0022183 A1 | 1/2019 | Lim et al. | |

FOREIGN PATENT DOCUMENTS

| | | | | |
|---|---|---|---|---|
| KR | 10-2017-0079409 A | 7/2017 | | |
| KR | 10-1808234 B1 | 12/2017 | | |
| KR | 10-1861163 B1 | 5/2018 | | |
| WO | WO-2011/041642 A1 | 4/2011 | | |
| WO | WO-2016208989 A1 * | 12/2016 | ........... | A61K 38/179 |
| WO | WO-2017066554 A1 * | 4/2017 | ........... | A61K 38/179 |
| WO | WO-2017129685 A1 * | 8/2017 | ........... | A61K 38/179 |
| WO | WO-2017-178544 A1 | 10/2017 | | |
| WO | WO-2018094316 A1 * | 5/2018 | ........... | A61K 38/179 |
| WO | WO-2019/099921 A2 | 5/2019 | | |

OTHER PUBLICATIONS

Bahrenburg, S., Karow, A.R. and Garidel, P. (2015), Buffer-free therapeutic antibody preparations provide a viable alternative to conventionally buffered solutions: From protein buffer capacity prediction to bioprocess applications. Biotechnology Journal, 10: 610-622. (Year: 2015).*
Perez-Ramirez, B., Geiger, C., Mezhebovsky, T., Bussemer, T. Approaches in subcutaneous delivery of monoclonal antibodies. European Pharmaceutical Review. 2016 4:1-5. (Year: 2016).*
Anonymous. PEG3350 Technical Data Sheet, CISCO, www.ciscochem.com; Jun. 3, 2015. (Year: 2015).*
Gillespie, C. What is the pH of a sugar solution? www.sciencing.com; Mar. 24, 2022 (Year: 2022).*
International Search Report from corresponding PCT Application No. PCT/KR2019/011762, dated Jan. 10, 2020.
Extended European Search Report from corresponding European Patent Application No. 19859105.9, issued on Jun. 9, 2022.

* cited by examiner

*Primary Examiner* — Daniel E Kolker
*Assistant Examiner* — Maureen Varina Driscoll
(74) *Attorney, Agent, or Firm* — Harness, Dickey & Pierce, P.L.C.

(57) ABSTRACT

The present invention relates to a protein-stabilized liquid formulation and provides: a composition for protein stabilization, the composition including a stabilizer and a surfactant and not including a buffer; a protein liquid composition including the composition for stabilization and a protein; and a method of producing a protein-stabilized liquid composition which uses the composition for stabilization.

12 Claims, 7 Drawing Sheets

Specification includes a Sequence Listing.

```
SEQUENCE LISTING

<160> NUMBER OF SEQ ID NOS: 1

<210> SEQ ID NO 1
<211> LENGTH: 431
<212> TYPE: PRT
<213> ORGANISM: Artificial
<220> FEATURE:
<223> OTHER INFORMATION: Synthetic (Aflibercept)

<400> SEQUENCE: 1

Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175
```

-continued

```
Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
            355                 360                 365

Asn Gly Gln Pro Glu Asn Asn Tyr Lys Thr Thr Pro Pro Val Leu Asp
    370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
                405                 410                 415

Leu His Asn His Tyr Thr Gln Lys Ser Leu Ser Leu Ser Pro Gly
            420                 425                 430
```

LIQUID COMPOSITION COMPRISING PROTEIN

CROSS-REFERENCE TO RELATED APPLICATIONS

This application is a national phase application of PCT Application No. PCT/KR2019/011762, filed on Sep. 10, 2019, which claims the benefit and priority to Korean Patent Application No. 10-2018-0107588, filed on Sep. 10, 2018. The entire disclosures of the applications identified in this paragraph are incorporated herein by references.

TECHNICAL FIELD

The present disclosure relates to a protein-stabilized liquid formulation, and more particularly, to a composition for protein stabilization, the composition including a stabilizer and a surfactant and not including a buffer; a protein liquid composition including the composition for stabilization and a protein; and a method of preparing a protein-stabilized liquid composition, the method uses the composition for stabilization.

BACKGROUND ART

Fusion protein drugs may cause physiochemical instability of the drugs due to their higher molecular weights and more complex structures than general protein drugs when the drugs are out of optimal conditions, and thus aggregation, fragments, and isomers of protein may likely be produced, resulting reduction in physiological activity of protein. In this regard, for protein drugs, it is important to develop an optimal formulation based on various conditions such as pH condition, buffer selection, a concentration of protein, and a type/concentration of an excipient.

Particularly, since the stability and activity of protein drugs depend on pH, maintaining the target pH during the shelf life of the drug is very important in terms of protein stability and efficacy. Therefore, it is common to use one or more buffering agents to achieve the target pH in the production (including preparation and formulation) of protein drugs.

The buffers in a protein drug composition needs to satisfy the following requirements: First, the buffer needs to be properly dissolved and must not be toxic or form harmful complexes with metal ions. Also, the buffer should not interact with other components in the composition and affect the stability and efficacy of protein. Also, the buffer needs to be stable and effective in maintaining pH during its formulation process or storage under the exposed conditions.

However, when a buffer is added to maintain pH, which is important for protein stability, there is a problem in that ionic strength may be increased depending on the added concentration and type of the buffer, thereby increasing the aggregation of protein. In fact, when EYLEA® is used, a problem of significant decrease in a stabilizing effect occurred due to an increase in protein aggregation under a sever condition of 40° C.

SUMMARY

Technical Problem

Provided are a composition for stabilization that increases protein stability and a pharmaceutical liquid composition of a stable protein, the liquid composition including the composition for stabilization.

According to an embodiment, provided is a composition for stabilization of protein, the composition including
    a stabilizer; and
    a surfactant.
A pH of the composition for stabilization may be in a range of 4 to 8 or, for example, 5.2 to 7.2, 5.5 to 7, 5.5 to 6.6, 5.5 to 6.4, 5.5 to 6.2, 5.8 to 7, 5.8 to 6.6, 5.8 to 6.4, 5.8 to 6.2, 5.7 to 6.7, or 5.9 to 6.5. The composition for stabilization may not include a buffer. The surfactant may include at least one selected from all non-ionic surfactants commonly used in protein formulation. The composition for stabilization may be an aqueous composition.

According to another embodiment, provided is a liquid composition including a protein; a stabilizer; and a surfactant. A pH of the liquid composition may be in a range of 4 to 8 or, for example, 5.2 to 7.2, 5.5 to 7, 5.5 to 6.6, 5.5 to 6.4, 5.5 to 6.2, 5.8 to 7, 5.8 to 6.6, 5.8 to 6.4, 5.8 to 6.2, 5.7 to 6.7, or 5.9 to 6.5. The liquid composition may not include a buffer. The liquid composition may be an aqueous liquid composition.

For example, the liquid composition may include
    (1) 5 mg/ml to 300 mg/ml of a protein;
    (2) a stabilizer; and
    (3) a surfactant,
    and a pH of the liquid composition may be in a range of 4 to 8 or, for example, 5.2 to 7.2, 5.5 to 7, 5.5 to 6.6, 5.5 to 6.4, 5.5 to 6.2, 5.8 to 7, 5.8 to 6.6, 5.8 to 6.4, 5.8 to 6.2, 5.7 to 6.7, or 5.9 to 6.5. The liquid composition may not include a buffer.
The liquid composition may include the stabilizer in an amount from 0.5% (w/v) to 50% (w/v) based on the total amount of the composition. The stabilizer may serve as an isotonic agent and may be, for example, at least one selected from the group consisting of polyols such as sugar alcohols and sugars. In one embodiment, the stabilizer may include at least one selected from the group consisting of trehalose, sucrose, mannitol, sorbitol, xylitol, glucose, and glycerol. In one embodiment, the stabilizer may not include sodium chloride. The liquid composition may be an aqueous liquid composition.

The liquid composition may include the surfactant in an amount from 0.01% (w/v) to 3% (w/v) based on the total amount of the composition. The surfactant may include at least one selected from all surfactants, such as non-ionic surfactants, commonly used in protein formulation.

According to another embodiment, provided is a pharmaceutical composition including the liquid composition. The pharmaceutical composition has a pharmacological activity corresponding to the activity of the protein in the liquid composition.

For example, in the liquid composition or the pharmaceutical composition, a molecular weight of the protein may be in a range of 10 kDa to 500 kDa, 10 kDa to 400 kDa, 10 kDa to 300 kDa, 10 kDa to 200 kDa, or 10 kDa to 150 kDa. In one embodiment, the protein may be a VEGF antagonist or, for example, at least one selected from the group consisting of aflibercept (having a molecular weight in a range of about 97 kDa to about 115 kDa), bevacizumab (having a molecular weight of about 149 kDa), and ranibizumab (having a molecular weight of about 48 kDa), but embodiments are not limited thereto.

When the protein is a VEGF antagonist or, for example, at least one selected from the group consisting of aflibercept, bevacizumab, ranibizumab and the like, the pharmaceutical composition may be an ophthalmic composition or, particularly, a parenteral formulation for intravitreal administration.

The liquid composition or pharmaceutical composition may be for intravitreal administration.

According to another embodiment, provided is a method of stabilizing protein or a method of preparing a protein-stabilized aqueous liquid composition, the method including mixing a protein with the stabilizer.

Solution to Problem

According to one or more embodiments of the present disclosure, provided are a composition for stabilization for enhancing stability of a protein, a protein-stabilized liquid composition including the composition for stabilization, and a method of preparing a stable liquid composition including a protein.

Generally, in the preparation of a protein drug composition, it is inevitable to use a buffer to adjust pH in a range preventing protein denaturation, but protein aggregation may occur due to an ion strength effect caused by the buffer, and stability of the protein formulation may be deteriorated. In particular, in case of preparing a protein formulation for ocular administration (e.g., intravitreal administration), an intraocular pressure may increase due to small particles formed by the protein aggregation, and a risk of inflammation occurrence may increase. Accordingly, an object of the present invention is to provide a formulation for stabilizing a protein, the formulation having a proper pH maintained and excellent formulation stability without including a buffer to minimize protein aggregation and physiochemical instability caused by a buffer.

According to an aspect of the present disclosure, provided is a composition for protein stabilization, the composition including a stabilizer; and a surfactant.

A pH of the composition for stabilization may be in a range of 4 to 8 or, for example, 5.2 to 7.2, 5.5 to 7, 5.5 to 6.6, 5.5 to 6.4, 5.5 to 6.2, 5.8 to 7, 5.8 to 6.6, 5.8 to 6.4, 5.8 to 6.2, 5.7 to 6.7, or 5.9 to 6.5. The composition for stabilization may not include a buffer. The surfactant may include at least one selected from all non-ionic surfactants commonly used in protein formulation. The composition for stabilization may be an aqueous composition.

According to another aspect of the present disclosure, provided is a liquid composition including a protein; a stabilizer; and a surfactant. A PH of the liquid composition may be in a range of 4 to 8 or, for example, 5.2 to 7.2, 5.5 to 7, 5.5 to 6.6, 5.5 to 6.4, 5.5 to 6.2, 5.8 to 7, 5.8 to 6.6, 5.8 to 6.4, 5.8 to 6.2, 5.7 to 6.7, or 5.9 to 6.5. The liquid composition may not include a buffer. The liquid composition may be an aqueous composition.

The protein liquid composition provided herein is characterized in that the composition may maintain pH, which is one of important factors that affect protein stability, in an appropriate range, while not including a buffer and has excellent protein stability in the composition (e.g., protein stability indication factors such as % HMW, % charge variant, and/or % main of the protein are excellent), and the pH maintaining and/or excellent protein stability characteristics may be repeatedly achieved.

For example, the liquid composition may include (1) 5 mg/ml to 300 mg/ml of a protein;

(2) a stabilizer; and (3) a surfactant, and a pH of the liquid composition may be in a range of 4 to 8 or, for example, 5.2 to 7.2, 5.5 to 7, 5.5 to 6.6, 5.5 to 6.4, 5.5 to 6.2, 5.8 to 7, 5.8 to 6.6, 5.8 to 6.4, 5.8 to 6.2, 5.7 to 6.7, or 5.9 to 6.5. The liquid composition may not include a buffer.

A protein amount in the liquid composition may be 300 mg/ml or less, 250 mg/ml or less, 200 mg/ml or less, 150 mg/ml or less, 125 mg/ml or less, 100 mg/ml or less, 90 mg/ml or less, 80 mg/ml or less, 70 mg/ml or less, 60 mg/ml or less, or 50 mg/ml or less, or, for example, in a range of 5 mg/ml to 300 mg/ml, 5 mg/ml to 250 mg/ml, 5 mg/ml to 200 mg/ml, 5 mg/ml to 150 mg/ml, 5 mg/ml to 125 mg/ml, 5 mg/ml to 100 mg/ml, 5 mg/ml to 90 mg/ml, 5 mg/ml to 80 mg/ml, 5 mg/ml to 70 mg/ml, 5 mg/ml to 60 mg/ml, 5 mg/ml to 50 mg/ml, 10 mg/ml to 300 mg/ml, 10 mg/ml to 250 mg/ml, 10 mg/ml to 200 mg/ml, 10 mg/ml to 150 mg/ml, 10 mg/ml to 125 mg/ml, 10 mg/ml to 100 mg/ml, 10 mg/ml to 90 mg/ml, 10 mg/ml to 80 mg/ml, 10 mg/ml to 70 mg/ml, 10 mg/ml to 60 mg/ml, 10 mg/ml to 50 mg/ml, 20 mg/ml to 300 mg/ml, 20 mg/ml to 250 mg/ml, 20 mg/ml to 200 mg/ml, 20 mg/ml to 150 mg/ml, 20 mg/ml to 125 mg/ml, 20 mg/ml to 100 mg/ml, 20 mg/ml to 90 mg/ml, 20 mg/ml to 80 mg/ml, 20 mg/ml to 70 mg/ml, 20 mg/ml to 60 mg/ml, 20 mg/ml to 50 mg/ml, 30 mg/ml to 300 mg/ml, 30 mg/ml to 250 mg/ml, 30 mg/ml to 200 mg/ml, 30 mg/ml to 150 mg/ml, 30 mg/ml to 125 mg/ml, 30 mg/ml to 100 mg/ml, 30 mg/ml to 90 mg/ml, 30 mg/ml to 80 mg/ml, 30 mg/ml to 70 mg/ml, 30 mg/ml to 60 mg/ml, or 30 mg/ml to 50 mg/ml.

Also, in one embodiment, an amount of the protein in the liquid composition may be in a range of 5 mg/ml to 50 mg/ml, 5 mg/ml to 49 mg/ml, 5 mg/ml to 48 mg/ml, 5 mg/ml to 47 mg/ml, 5 mg/ml to 46 mg/ml, 5 mg/ml to 45 mg/ml, 5 mg/ml to 44 mg/ml, 5 mg/ml to 43 mg/ml, 5 mg/ml to 42 mg/ml, 5 mg/ml to 41 mg/ml, 10 mg/ml to 50 mg/ml, 10 mg/ml to 49 mg/ml, 10 mg/ml to 48 mg/ml, 10 mg/ml to 47 mg/ml, 10 mg/ml to 46 mg/ml, 10 mg/ml to 45 mg/ml, 10 mg/ml to 44 mg/ml, 10 mg/ml to 43 mg/ml, 10 mg/ml to 42 mg/ml, 10 mg/ml to 41 mg/ml, 20 mg/ml to 50 mg/ml, 20 mg/ml to 49 mg/ml, 20 mg/ml to 48 mg/ml, 20 mg/ml to 47 mg/ml, 20 mg/ml to 46 mg/ml, 20 mg/ml to 45 mg/ml, 20 mg/ml to 44 mg/ml, 20 mg/ml to 43 mg/ml, 20 mg/ml to 42 mg/ml, 20 mg/ml to 41 mg/ml, 30 mg/ml to 50 mg/ml, 30 mg/ml to 49 mg/ml, 30 mg/ml to 48 mg/ml, 30 mg/ml to 47 mg/ml, 30 mg/ml to 46 mg/ml, 30 mg/ml to 45 mg/ml, 30 mg/ml to 44 mg/ml, 30 mg/ml to 43 mg/ml, 30 mg/ml to 42 mg/ml, or 30 mg/ml to 41 mg/ml.

In one embodiment, a pH of the liquid composition may be in a range of 4 to 8 or, for example, 5.2 to 7.5, 5.2 to 7.2, 5.2 to 7, 5.2 to 6.8, 5.2 to 6.6, 5.2 to 6.5, 5.2 to 6.4, 5.2 to 6.2, 5.5 to 7.5, 5.5 to 7.2, 5.5 to 7, 5.5 to 6.8, 5.5 to 6.7, 5.5 to 6.6, 5.5 to 6.5, 5.5 to 6.4, 5.5 to 6.2, 5.7 to 7.5, 5.7 to 7.2, 5.7 to 7, 5.7 to 6.8, 5.7 to 6.7, 5.7 to 6.6, 5.7 to 6.5, 5.7 to 6.4, 5.7 to 6.2, 5.8 to 7.5, 5.8 to 7.2, 5.8 to 7, 5.8 to 6.8, 5.8 to 6.7, 5.8 to 6.6, 5.8 to 6.5, 5.8 to 6.4, 5.8 to 6.2, 5.9 to 7.5, 5.9 to 7.2, 5.9 to 7, 5.9 to 6.8, 5.9 to 6.7, 5.9 to 6.6, 5.9 to 6.5, 5.9 to 6.4, 5.9 to 6.3, 5.9 to 6.2, or 6.2.

The liquid composition provided herein may be characterized in enhancing stability of a protein by not including a buffer, which causes protein aggregation. The buffer not included in ingredients of the liquid composition may be at least one selected from buffers having a commonly used buffering capacity, and examples of the buffer may include (1) at least one acid selected from the group consisting of phosphoric acid, acetic acid, citric acid, succinic acid, carbonic acid and the like; (2) a pharmaceutically acceptable salt of the acid (e.g., a sodium salt, a potassium salt, etc.); (3) at least one amino acid selected from the group consisting of histidine, aspartic acid, glutamic acid and the like; and (4) a pharmaceutically acceptable salt (e.g., a hydrochloride or acetate such as histidine-HCl, histidine-acetate, etc.) of the amino acid. Thus, the liquid composition may not include at least one selected from the group consisting of phosphoric acid, acetic acid, citric acid, succinic acid, carbonic acid, a pharmaceutically acceptable salt (e.g., a sodium salt or a potassium salt) of any of the acids (phosphoric acid, acetic acid, citric acid, succinic acid, and carbonic acid), histidine, aspartic acid, glutamic acid, and a pharmaceutically acceptable salt (e.g., histidine-HCl or histidine-acetate) of any of the amino acids (histidine, aspartic acid, and glutamic acid).

The liquid composition may include the stabilizer in an amount from 0.5% (w/v) to 50% (w/v) based on the total amount of the composition. The stabilizer may serve as an isotonic agent and may be, for example, at least one selected from the group consisting of polyols such as sugar alcohols and sugars. In some embodiments, the stabilizer may be at least one selected from the group consisting of trehalose, sucrose, mannitol, sorbitol, xylitol, glucose, and glycerol. For example, the stabilizer may include at least one selected from the group consisting of 1 to 20% (w/v), 1 to 15% (w/v), 1 to 10% (w/v), 5 to 20% (w/v), 5 to 15% (w/v), 5 to 10% (w/v), 5.5 to 20% (w/v), 5.5 to 15% (w/v), 5.5 to 10% (w/v), 6 to 20% (w/v), 6 to 15% (w/v), 6 to 10% (w/v), 7 to 20% (w/v), 7 to 15% (w/v), 7 to 10% (w/v), 7.8 to 20% (w/v), 7.8 to 15% (w/v), 7.8 to 10% (w/v), 7.8 to 8.2% (w/v), or 8% (w/v) of trehalose; 1 to 20% (w/v), 1 to 15% (w/v), 1 to 10% (w/v), 5 to 20% (w/v), 5 to 15% (w/v), 5 to 10% (w/v), 5.5 to 20% (w/v), 5.5 to 15% (w/v), 5.5 to 10% (w/v), 6 to 20% (w/v), 6 to 15% (w/v), 6 to 10% (w/v), 7 to 20% (w/v), 7 to 15% (w/v), 7 to 10% (w/v), 7.8 to 20% (w/v), 7.8 to 15% (w/v), 7.8 to 10% (w/v), 7.8 to 8.2% (w/v), or 8% (w/v) of sucrose; and 0.5 to 10% (w/v), 0.5 to 7.5% (w/v), 0.5 to 5% (w/v), 1 to 10% (w/v), 1 to 7.5% (w/v), 1 to 5% (w/v), 3 to 10% (w/v), 3 to 7.5% (w/v), 3 to 5% (w/v), 4 to 5% (w/v), or 4.5% (w/v) of mannitol.

In some embodiments, the stabilizer may not include sodium chloride. In this regard, since the protein liquid composition provided herein does not include sodium chloride as a stabilizer, stability of a protein may further be enhanced (e.g., Δ% HMW decreased).

In some embodiments, the liquid composition may include the surfactant in an amount from 0.001 to 3% (w/v), 0.001 to 2% (w/v), 0.001 to 1% (w/v), 0.001 to 0.5% (w/v), 0.001 to 0.1% (w/v), 0.001 to 0.05% (w/v), 0.01 to 3% (w/v), 0.01 to 2% (w/v), 0.01 to 1% (w/v), 0.01 to 0.5% (w/v), 0.01 to 0.1% (w/v), 0.01 to 0.05% (w/v), or 0.03% (w/v). The surfactant may be selected from all pharmaceutically acceptable surfactants capable of evenly dispersing the protein in a medium of the liquid composition. The surfactant may be a non-ionic surfactant and may be at least one selected from the group consisting of polysorbates (e.g., polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), where the figure, (20), after "polyoxyethylene" represents the total number of oxyethylene groups ($-(CH_2CH_2O)-$)), poloxamers (PEO-PPO-PEO copolymer; where PEO: poly(ethylene oxide), and PPO: poly(propylene oxide)), polyethylene-polypropylene glycols, polyoxyethylene compounds (e.g., polyoxyethylene-stearate, polyoxyethylene alkyl ether (alkyl: $C_1$-$C_{30}$), polyoxyethylene monolyryl ether, alkylphenyl polyoxyethylene copolymer (alkyl: $C_1$-$C_{30}$), and sodium dodecyl sulphate (SDS). For example, the surfactant may be polysorbates (e.g., polysorbate 20).

The liquid composition may include the protein, the stabilizer, and the surfactant in the above-described amounts and may include an aqueous medium (e.g., water (purified water), physiological saline, or water for injection) in a residual amount of the liquid composition.

The liquid composition provided herein may be isotonic with the human body fluid. For example, an osmotic pressure of the liquid composition may be in a range of about 200 mOsm/kg to about 400 mOsm/kg, about 200 mOsm/kg to about 350 mOsm/kg, about 200 mOsm/kg to about 300 mOsm/kg, about 250 mOsm/kg to about 400 mOsm/kg, about 250 mOsm/kg to about 350 mOsm/kg, or about 250 mOsm/kg to about 300 mOsm/kg or, for example, may be in a range of about 270 mOsm/kg to about 290 mOsm/kg. The osmotic pressure may be adjusted by the stabilizer.

An electrical conductivity of the liquid composition provided herein may be about 0 mS/cm or more (or more than about 0 mS/cm), about 0.0001 mS/cm or more, or about 0.001 mS/cm or more, for example, in a range of about 0 mS/cm to about 10 mS/cm, about 0 mS/cm to about 7 mS/cm, about 0 mS/cm to about 5 mS/cm, about 0 mS/cm to about 2.5 mS/cm, about 0 mS/cm to about 1 mS/cm, about 0 mS/cm to about 0.5 mS/cm, about 0 mS/cm to about 0.1 mS/cm, about 0 mS/cm to about 0.05 mS/cm, more than about 0 mS/cm to not more than about 10 mS/cm, more than about 0 mS/cm to not more than about 7 mS/cm, more than about 0 mS/cm to not more than about 5 mS/cm, more than about 0 mS/cm to not more than about 2.5 mS/cm, more than about 0 mS/cm to not more than about 1 mS/cm, more than about 0 mS/cm to not more than about 0.5 mS/cm, more than about 0 mS/cm to not more than about 0.1 mS/cm, more than about 0 mS/cm to not more than about 0.05 mS/cm, about 0.0001 mS/cm to about 10 mS/cm, about 0.0001 mS/cm to about 7 mS/cm, about 0.0001 mS/cm to about 5 mS/cm, about 0.0001 mS/cm to about 2.5 mS/cm, about 0.0001 mS/cm to about 1 mS/cm, about 0.0001 mS/cm to about 0.5 mS/cm, about 0.0001 mS/cm to about 0.1 mS/cm, about 0.0001 mS/cm to about 0.05 mS/cm, about 0.001 mS/cm to about 10 mS/cm, about 0.001 mS/cm to about 7 mS/cm, about 0.001 mS/cm to about 5 mS/cm, about 0.001 mS/cm to about 2.5 mS/cm, about 0.001 mS/cm to about 1 mS/cm, about 0.001 mS/cm to about 0.5 mS/cm, about 0.001 mS/cm to about 0.1 mS/cm, or about 0.001 mS/cm to about 0.05 mS/cm.

In the liquid composition provided herein, the protein may be a protein drug or, for example, a protein (e.g., fusion protein) having a molecular weight in a range of 10 to 500 kDa, 10 to 400 kDa, 10 to 300 kDa, 10 to 200 kDa, or 10 to 150 kDa. In some embodiments, the protein may be a vascular endothelial growth factor (VEGF) antagonist, for example, a VEGF-specific fusion protein, in which a VEGF binding site derived from an extracellular domain of human VEGF receptor 1 and VEGF receptor 2 and the Fc region of human IgG1 are fused. In some embodiments, the VEGF-specific fusion protein may be a fusion protein, in which a site including immunoglobulin-like (Ig) domain 2 of human VEGF receptor 1 (Flt1) and Ig domain 3 of human VEGF receptor 2 (Flt1 or Flt4) and the Fc region of human IgG1 are fused, and may be, for example, aflibercept having an amino acid sequence of SEQ ID NO: 1 as follows.

Aflibercept amino acid sequence (SEQ ID NO: 1)
SDTGRPFVEM YSEIPEIIHM TEGRELVIPC RVT-SPNITVT LKKFPLDTLI PDGKRIIWDS RKGFIIS-NAT YKEIGLLTCE ATVNGHLYKT NYLTHRQTNT IIDVVLSPSH GIELSVGEKL VLNCTARTEL NVGIDENWEY PSSKHQHKKL VNRDLKTQSG SEMKKFLSTL TIDGVTRSDQ

7

GLYTCAASSG LMTKKNSTFV RVHEKDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP G (Disulfide bridge: 30-79; 124-185; 246-306; 352-410, Dimer: 211; 214)

The protein in the liquid composition may be produced recombinantly or synthetically.

The liquid composition provided herein may be maintained stable at a high temperature of about 40° C. for 4 weeks or more and/or maintained stable under severe conditions such as at least 1 cycle (e.g., at least 2 cycles, at least 3 cycles, at least 4 cycles, or at least 5 cycles) of freeze/thaw condition, vibration condition (at least 100 rpm (e.g., at least 200 rpm, at least 300 rpm, or at least 400 rpm), and at least for 24 hours (e.g., at least 36 hours, at least 48 hours, at least 60 hours, or at least 72 hours).

The term "excellent stability" or "maintained stable" may refer to a structure and/or physical, chemical, and/or biological characteristics of a protein in a composition being maintained during storage of the composition (e.g., low protein polymer formation rate, low protein aggregation rate, low protein decomposition rate, and/or low denaturation rate during the storage). Various analytical techniques of measuring protein stability are well known in the art.

For example, when an amount of protein (e.g., fusion protein) in the liquid composition provided herein is 40 mg/ml (pH 6.2), an amount of change (% HMW at 4th week of the storage—% HMW at 0th week (initial) of the storage) of a protein polymer formation rate or aggregation rate (High Molecular Weight % (w/v); % HMW) measured while storing the composition at a temperature of about 40° C. for 4 weeks using a size exclusion chromatography (SEC) may be lower than about 9%, for example, about 8% or lower, about 7% or lower, about 6% or lower, about 5.5% or lower, about 5% or lower, about 4.5% or lower, or about 4% or lower (e.g., in a range of about 0.1% to about 8%, about 0.5% to about 8%, about 1% to about 8%, about 1.5% to about 8%, about 2% to about 8%, about 2.5% to about 8%, about 3% to about 8%, about 3.5% to about 8%, about 0.1% to about 7%, about 0.5% to about 7%, about 1% to about 7%, about 1.5% to about 7%, about 2% to about 7%, about 2.5% to about 7%, about 3% to about 7%, about 3.5% to about 7%, about 0.1% to about 6%, about 0.5% to about 6%, about 1% to about 6%, about 1.5% to about 6%, about 2% to about 6%, about 2.5% to about 6%, about 3% to about 6%, about 3.5% to about 6%, about 0.1% to about 5.5%, about 0.5% to about 5.5%, about 1% to about 5.5%, about 1.5% to about 5.5%, about 2% to about 5.5%, about 2.5% to about 5.5%, about 3% to about 5.5%, about 3.5% to about 5.5%, about 0.1% to about 5%, about 0.5% to about 5%, about 1% to about 5%, about 1.5% to about 5%, about 2% to about 5%, about 2.5% to about 5%, about 3% to about 5%, about 3.5% to about 5%, about 0.1% to about 4.5%, about 0.5% to about 4.5%, about 1% to about 4.5%, about 1.5% to about 4.5%, about 2% to about 4.5%, about 2.5% to about 4.5%, about 3% to about 4.5%, about 3.5% to about 4.5%, about 0.1% to about 4%, about 0.5% to about 4%, about 1% to about 4%, about 1.5% to about 4%, about 2% to about 4%, about 2.5% to about 4%, about 3% to about 4%, or about 3.5% to about 4%), but embodiments are not limited thereto.

In some embodiments, when an amount of protein (e.g., fusion protein) in the liquid composition provided herein is 40 mg/ml (pH 6.2), an amount of change (% HMW after 5 cycles of freeze/thaw—initial % HMW) of a protein polymer formation rate or aggregation rate (High Molecular Weight % (w/v); % HMW) measured using a common SEC after preforming 5 cycles of freeze/thaw (where in each cycle: freeze at −70° C. for 18 hours+thaw at room temperature (25° C.) for 1 to 2 hours) may be lower than about 0.15%, for example, about 0.13% or lower, about 0.1% or lower, about 0.08% or lower, about 0.06% or lower, about 0.05% or lower, about 0.04% or lower, or about 0.03% or lower (where a lower limit may be about 0.001%, about 0.005%, or about 0.01%), but embodiments are not limited thereto.

In some embodiments, when the liquid composition provided herein includes 40 mg/ml of aflibercept (pH 6.2), a relative potency activity (% RPA) change (% RPA at 4th week—initial % RPA) with respect to VEGF of aflibercept measured while storing the composition at a temperature of about 40° C. for 4 weeks may be in a range of about −10% to about 10%, about −10% to about 7%, about −10% to about 5%, about-10% to about 4%, about −10% to about 3%, about −7% to about 10%, about −7% to about 7%, about −7% to about 5%, about −7% to about 4%, about −7% to about 3%, about −6% to about 10%, about −6% to about 7%, about −6% to about 5%, about −6% to about Δ%, about −6% to about 3%, about −5% to about 10%, about −5% to about 7%, about −5% to about 5%, about −5% to about 4%, or about −5% to about 3%, but embodiments are not limited thereto.

According to another embodiment, provided is a pharmaceutical composition including the liquid composition. The pharmaceutical composition may have an effect of preventing or treating ophthalmic diseases. In this regard, according to another embodiment, provided is a pharmaceutical composition for preventing or treating ophthalmic diseases, the pharmaceutical composition including the liquid composition. The ophthalmic diseases may be selected from all ophthalmic diseases caused by abnormal angiogenesis, and an example of the ophthalmic diseases may be selected from the group consisting of retinal vein occlusion (retinal vein obstructive macular edema), diabetic macular edema, diabetic retinopathy, choroidal neovascularization, age-related macular degeneration, retinal edema, and ocular ischemic syndrome (retinal ischemic syndrome). The ophthalmic disease may be a disease occurring in mammals such as humans.

According to another embodiment, provided is a method of preventing or treating an ophthalmic disease, the method including administering the liquid composition to a subject in need thereof. The administering of the liquid composition may be performed by intraocular administration (injection) or, for example, by intravitreal administration (injection). The subject may be selected from mammals including humans. Compositions of the liquid composition, types of protein (e.g., a VEGF antagonist) in the liquid composition, and ophthalmic diseases are the same as described above. According to another embodiment, provided is a method of intraocularly or intravitreally delivering the liquid composition or a protein in the liquid composition (e.g., a VEGF antagonist) or a method of enhancing intraocular or intravitreal delivery of the liquid composition or a protein (e.g., a VEGF antagonist) in the liquid composition, the method including intraocularly or intravitreally administering the liquid composition.

The pharmaceutical composition may further include a pharmaceutically acceptable carrier, diluent, and/or excipient. The pharmaceutically acceptable carrier may be that commonly used in the art, which may include at least one selected from the group consisting of lactose, dextrose, sucrose, sorbitol, mannitol, starch, acacia rubber, calcium phosphate, alginate, gelatin, calcium silicate, microcrystalline cellulose, polyvinylpyrrolidone, cellulose, water (e.g., purified water), physiological saline, syrup, methyl cellulose, methyl hydroxy benzoate, propyl hydroxy benzoate, talc, magnesium stearate, and mineral oil, but embodiments are not limited thereto.

The liquid composition or pharmaceutical composition may be for administration to mammals such as humans.

The liquid composition or pharmaceutical composition may be administered via oral or parenteral routes. An example of the parenteral administration (e.g., injection) may be intraocular administration (e.g., intravitreal administration), intravenous administration, subcutaneous administration, intramuscular administration, intraperitoneal administration, endothelial administration, topical administration, intranasal administration, intrapulmonary administration, intrarectal administration, or intratumoral administration or, for example, intravitreal administration.

In one embodiment, the liquid composition or pharmaceutical composition may be an ophthalmic composition including the VEGF antagonist described above, and, in this case, the composition may be an injection for intravitreal administration.

According to another embodiment, provided is a method of stabilizing protein or a method of preparing stabilized liquid composition, the method including mixing a protein with the composition for stabilization.

In one embodiment, provided is a method of stabilizing a protein or a method of preparing a stabilized aqueous liquid composition, the method including mixing (1) a protein;

(2) a stabilizer; and (3) a surfactant.

The method is characterized in that the method does not include mixing a buffer.

Types and amounts of ingredients used in the method of stabilizing a protein or the method of preparing a stabilized aqueous liquid composition are the same as described above.

Advantageous Effects of Disclosure

According to one or more embodiments, provided is a protein liquid formulation not including a buffer, which may provide a corresponding protein for a relatively extended period of time even under severe conditions as an effect of the protein liquid formulation suppressing decrease in physiological activity due to aggregation, degradation, or isomerization of the protein is equal to or superior to those of a formulation and a commercial formulation (e.g., EYLEA®) including a buffer of the related art.

DETAILED DESCRIPTION

Figure 1:
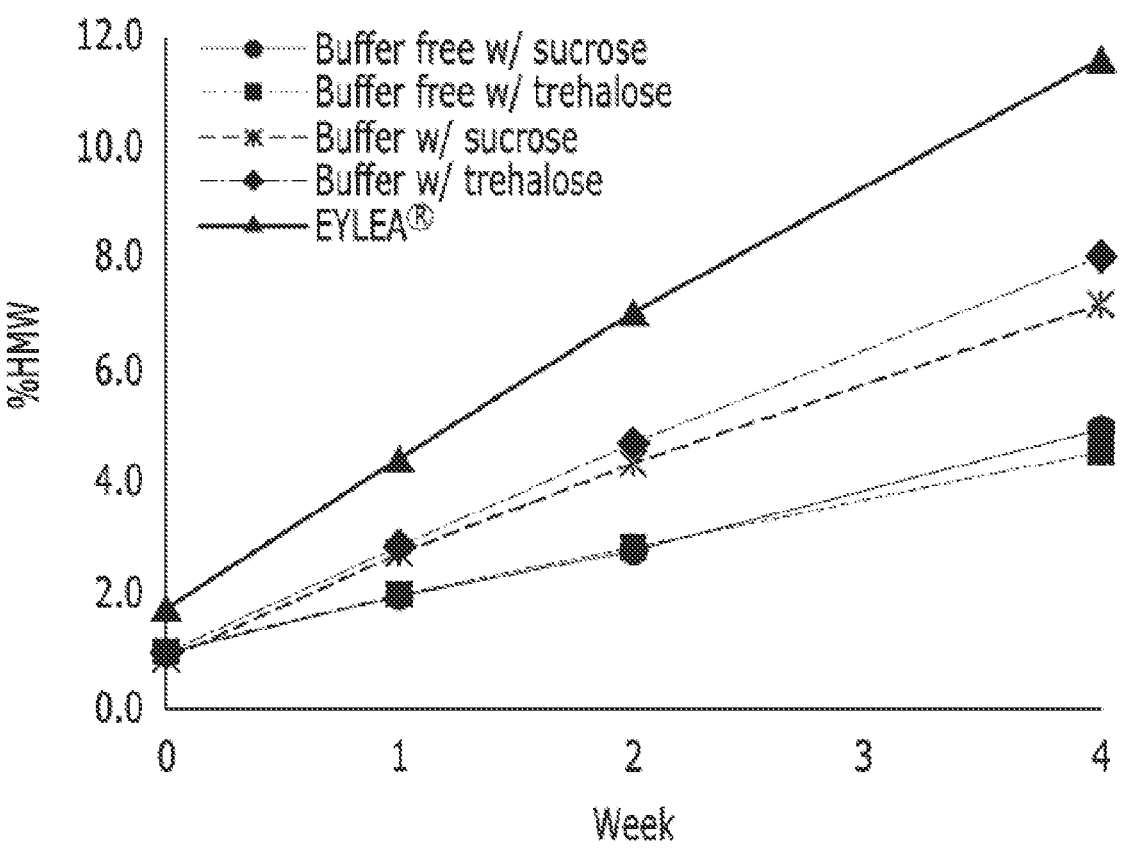
FIG. 1 is a graph showing a high-molecular weight % (% HMW) change rate (Δ% HMW) of a test formulation measured in Example 3 for 4 weeks after storing the test formulation at a temperature of 40° C. for 4 weeks.

Hereinafter, the present invention will be descried in more detail through examples and test examples. However, these examples and test examples are intended to illustrate the present invention and should not be construed as limiting the present invention.

Example 1. Preparation of Liquid Composition

Liquid formulations of a protein drug of compositions in Table 1 were prepared using a fusion protein, aflibercept (a fusion protein of a VEGF binding site derived from an extracellular domain of human VEGF receptors 1 and 2 and the Fc site of human IgG1; CAS Number: 862111-32-8; SEQ ID NO: 1), which functions a VEGF antagonist as a protein drug:

TABLE 1

| Formulation | Protein concentration | pH | Buffer | Stabilizer | Surfactant |
|---|---|---|---|---|---|
| Formulation 1 (Buffer-free w/sucrose) | 40 mg/ml | 6.2 | Not included | 8 % (w/v) Sucrose | 0.03 % (w/v) PS20 |
| Formulation 2 (Buffer-free w/ trehalose) | 40 mg/ml | 6.2 | Not included | 8 % (w/v) Trehalose | 0.03 % (w/v) PS20 |
| Formulation 3 (Buffer w/ sucrose) | 40 mg/ml | 6.2 | 10 mM sodium phosphate | 8% (w/v) Sucrose | 0.03 % (w/v) PS20 |
| formulation 4 (Buffer w/ trehalose) | 40 mg/ml | 6.2 | 10 mM sodium phosphate | 8 % (w/v) Trehalose | 0.03 % (w/v) PS20 |
| EYLEA ® (control) | 40 mg/ml | 6.2 | 10 mM sodium phosphate | 5 % (w/v) Sucrose, 40 mM NaCl | 0.03 % (w/v) PS20 |

(PS20: Polysorbate 20)

Example 2. Measurement of pH

To confirm the stability in terms of pH of a liquid formulation not including a buffer as prepared in Example 1, a pH of the liquid formulation was measured while being stored at 40° C. for 4 weeks, and to confirm the reproducibility, two identical liquid formulations were additionally prepared, and pH of each of the formulations was further measured at 40° C. for 4 weeks under the conditions of F/T 5 cycles and agitation. The resulting pH values (initial pH, PH at 4th week, pH after F/T 5 cycles, pH after agitation, and pH (corresponding condition pH—initial pH)) are shown in Table 2.

TABLE 2

| Formulation | pH | | | | pH | | |
| | Initial | 40° C./4 Wk | F/T 5 Cycles | Agitation | 40° C./4 Wk | F/T 5 Cycles | Agitation |
|---|---|---|---|---|---|---|---|
| Formulation 1 (N = 3) | 6.0 [SD:0.04] | 6.1 [SD:0.09] | N/A | N/A | 0.1 [SD:0.097] | N/A | N/A |
| Formulation 2 (N = 3) | 5.9 [SD:0.02] | 6.0 [SD:0.03] | N/A | N/A | 0.0 [SD:0.04] | N/A | N/A |
| Additional formulation 1 (N = 3) | 6.1 [SD:0.02] | 6.1 [SD:0.02] | 6.1 [SD:0.02] | 6.1 [SD:0.03] | 0.0 [SD:0.01] | 0.0 [SD:0.03] | 0.0 [SD:0.01] |
| Additional formulation 2 (N = 3) | 6.1 [SD:0.04] | 6.0 [SD:0.07] | 6.1 [SD:0.05] | 6.0 [SD:0.03] | 0.0 [SD:0.06] | 0.0 [SD:0.04] | 0.0 [SD:0.02] |

As shown in Table 2, Formulations 1 and 2 not including a buffer under the condition of a protein drug concentration of 40 mg/ml had no significant change in pH as compared with those of the initial states under the conditions of a thermal stress (40° C./4 wk), F/T cycles, and agitation. This results indicate that the pH may be maintained in a desired range and that the pH maintaining effect may be repeatedly achieved even when the formulation of the present invention does not include a buffer having a buffering effect of maintaining pH, which is the most important factor in terms of protein stability.

Example 3. Measurement of HMW Amount (%) (40° C.)

To test stability of the liquid formulation prepared in Example 1, an HMW amount (%) (% HMW; % high molecular weight; by weight) indicating a degree of aggregation of a protein drug in the formulation was measured while storing the formulation under the conditions of a protein drug concentration of 40 mg/ml, pH 6.2, and 40° C. for 4 weeks using a size-exclusion high-performance liquid chromatography (SE-HPLC).

In particular, a material being detected before a time when a monomer is detected is defined as HMW, and % HMW was measured using HPLC (Waters 2695 separation module alliance) and a column (Tosoh, TSK-gel G3000 SWXL) under the conditions of a flow rate of 1.0 mL/min and an injection time of 17 min (% HMW=$Area_H$/$Area_{TOTAL} \times 100$).

Thus measured % HMWs (initial % HMW, % HMW at $1^{st}$ week, % HMW at $2^{nd}$ week, % HMW at $4^{th}$ week, and Δ% HMW (% HMW at the corresponding week—initial % HMW)) are shown in Table 3 and FIG. 1:

As shown in Table 3 and FIG. 1, Δ% HMW reducing effects based on SE-HPLC analysis of Formulations 1 to 4 under the conditions of a protein drug concentration of 40 mg/ml and pH 6.2 were excellent as compared with that of EYLEA®. In particular, it was confirmed that the Δ% HMW reducing effects of Formulations 1 and 2 not including a buffer were more excellent than those of Formulations 3 and 4 including a buffer.

Example 4. Measurement of Acidic Amount (%) and Main Amount (%)

To test stability of the formulation prepared in Example 1, % Acidic (amount of % Acidic variants; by weight) and % Main (amount of the form maintaining a surface charge of an initial state in terms of charge variants (by weight)) indicating a degree of denaturation of a protein drug in the formulation were measured using an imaged capillary isoelectric focusing (icIEF) while storing the formulation under the condition of 40 mg/ml, pH 6.2, and a temperature of 40° C. for 4 weeks (wk).

In particular, % Acidic was measured by analyzing an acidic isoform of an incubated sample after treating with an enzyme (Sialidase A, Sigma-Aldrich) using icIEF instrument (Protein simple, iCE3) under the conditions of a sample injection duration of 110 sec and a sample injection pressure of 2000 psi.

Figure 2:
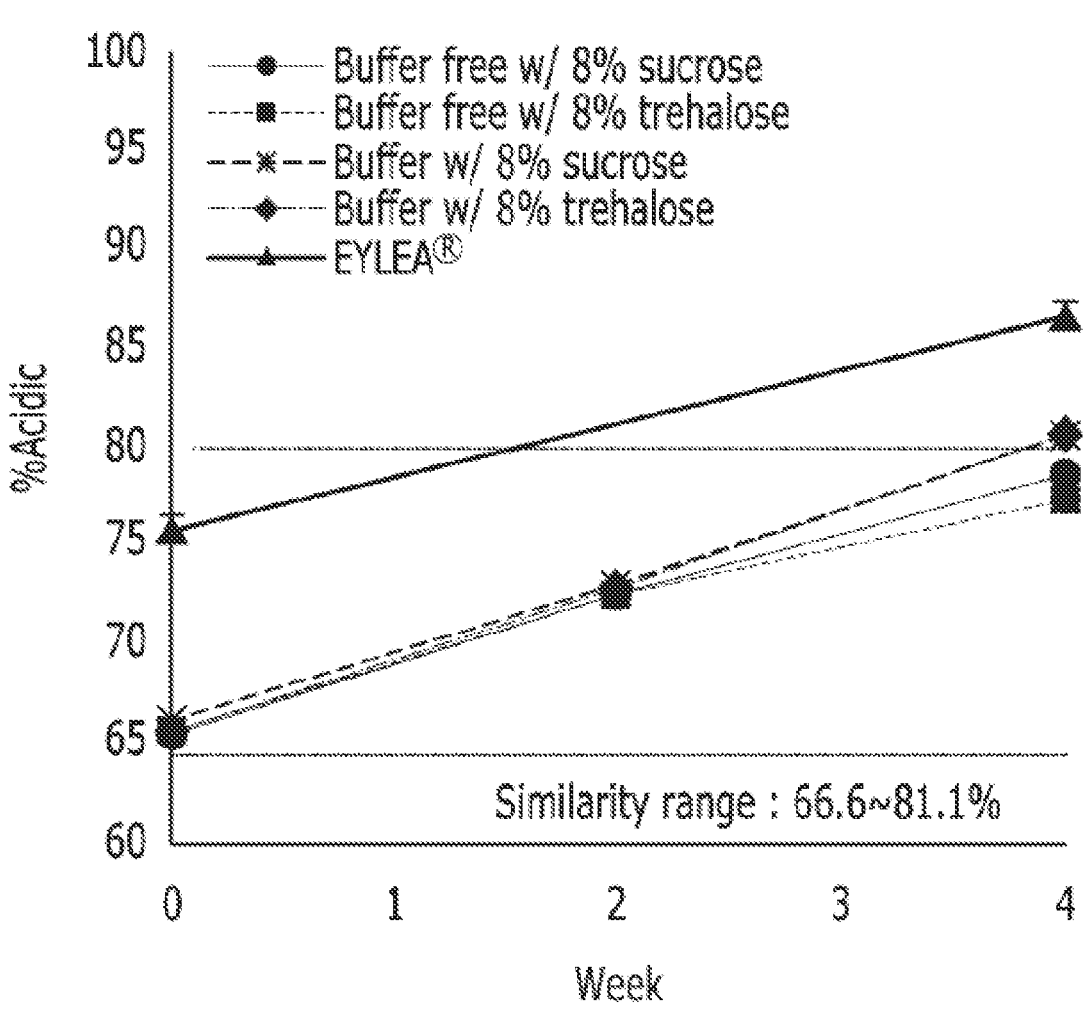
FIG. 2 is a graph showing a % Acidic change rate (Δ% Acidic) of a test formulation measured in Example 4 for 4 weeks after storing the test formulation at a temperature of 40° C. for 4 weeks.

The measured % Acidic (initial % Acidic, % Acidic at $4^{th}$ wk, and Δ% Acidic (% Acidic at $4^{th}$ wk—initial % Acidic)) are shown in Table 4 and FIG. 2:

TABLE 3

| Formulation | Initial % HMW | 40° C./1 wk % HMW | 40° C./1 wk Δ % HMW | 40° C./2 wk % HMW | 40° C./2 wk Δ % HMW | 40° C./4 wk % HMW | 40° C./4 wk Δ % HMW |
|---|---|---|---|---|---|---|---|
| Formulation 1 (N = 3) | 1.04 [SD:0.00] | 2.09 [SD:0.07] | 1.05 [SD:0.07] | 2.89 [SD:0.10] | 1.85 [SD:0.10] | 4.96 [SD:0.18] | 3.92 [SD:0.18] |
| Formulation 2 (N = 3) | 1.05 [SD:0.02] | 2.07 [SD:0.02] | 1.02 [SD:0.02] | 2.87 [SD:0.03] | 1.81 [SD:0.04] | 4.60 [SD:0.23] | 3.55 [SD:0.22] |
| Formulation 3 (N = 3) | 0.81 [SD:0.09] | 2.70 [SD:0.08] | 1.88 [SD:0.03] | 4.22 [SD:0.14] | 3.42 [SD:0.05] | 7.06 [SD:0.14] | 6.25 [SD:0.05] |
| Formulation 4 (N = 3) | 0.84 [SD:0.07] | 2.84 [SD:0.07] | 1.98 [SD:0.02] | 4.53 [SD:0.15] | 3.69 [SD:0.08] | 7.63 [SD:0.43] | 6.79 [SD:0.36] |
| EYLEA ® (N = 3) | 1.81 [SD:0.03] | 4.48 [SD:0.03] | 2.67 [SD:0.01] | 7.06 [SD:0.06] | 5.26 [SD:0.04] | 11.57 [SD:0.02] | 9.76 [SD:0.06] |

TABLE 4

| Formulation | Initial % Acidic | 40° C./4 Wk % Acidic | 40° C./4 Wk Δ % Acidic |
|---|---|---|---|
| Formulation 1 (N = 1) | 65.4 | 78.7 | 13.3 |
| Formulation 2 (N = 1) | 65.6 | 77.5 | 11.9 |
| Formulation 3 (N = 3) | 66.5 [SD: 1.25] | 80.5 [SD: 1.05] | 14.0 [SD: 0.69] |
| Formulation 4 (N = 3) | 65.7 [SD: 1.40] | 80.8 [SD: 0.97] | 15.2 [SD: 1.28] |
| EYLEA ® (N = 3) | 76.1 [SD: 0.70] | 86.6 [SD: 0.86] | 10.5 [SD: 0.97] |

Figure 3A:
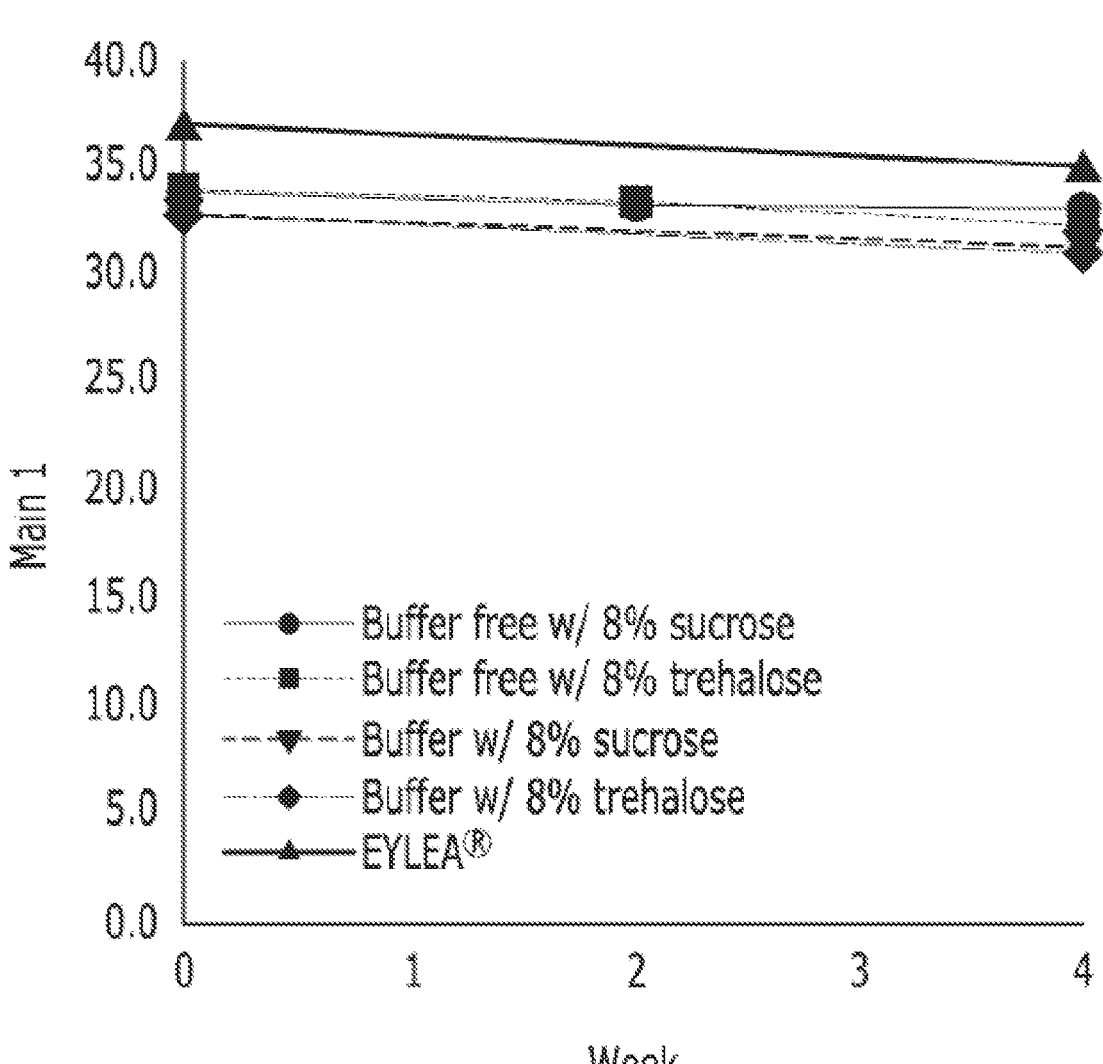
FIGS. 3A and 3B are each a graph showing a % Main change rate (Δ% Main1 and % Main2) of the test formulation measured in Example 4 for 4 weeks after storing the test formulation at a temperature of 40° C. for 4 weeks.
Figure 3B:
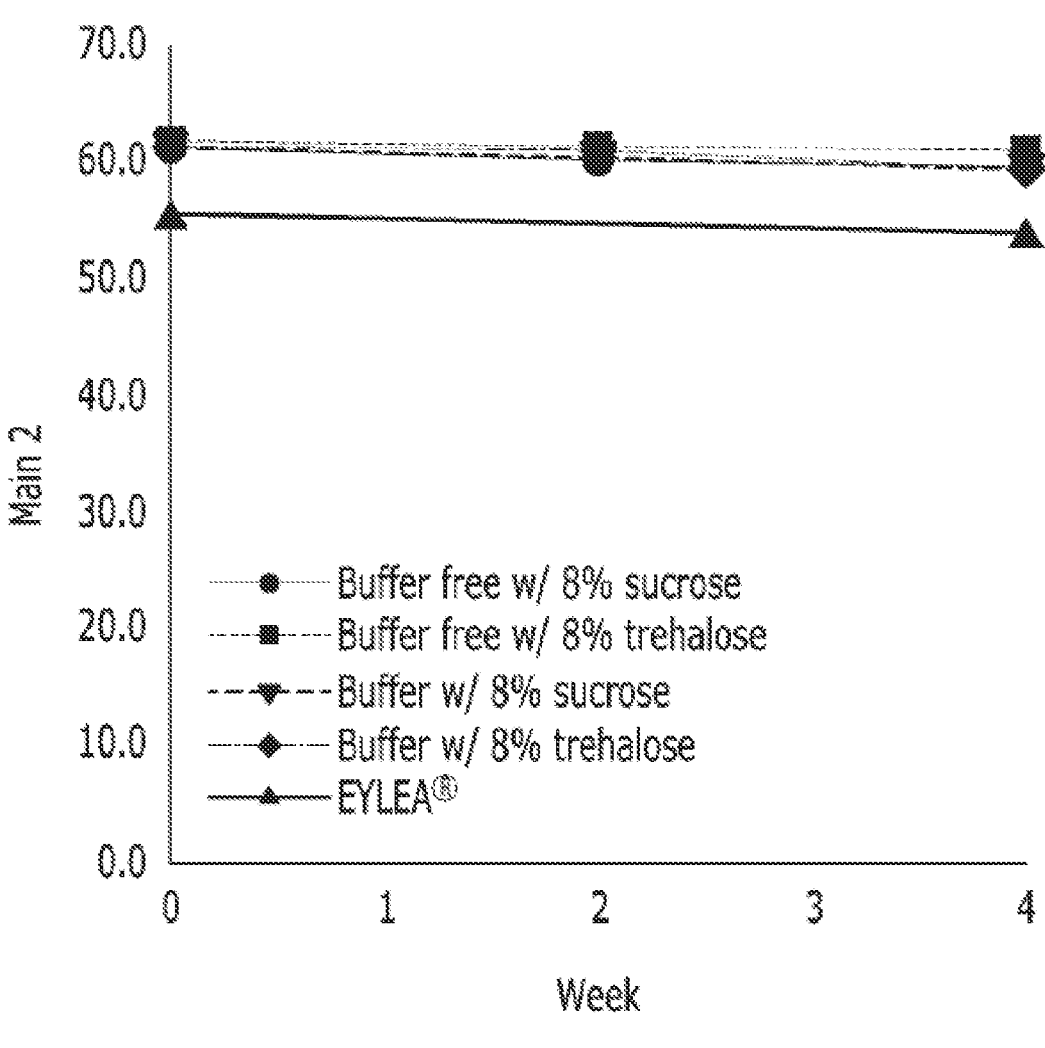

As shown in Table 4 and FIG. 2, acidic amount (%) increase rates based on icIEF analysis of Formulations 1 and 2 not including a buffer under the conditions of a protein drug concentration of 40 mg/ml and pH 6.2 were significantly low as compared with those of Formulations 3 and 4 including a buffer, and had no significant difference with the control formulation, EYLEA®, which is a commercial formulation. % Main was measured using capillary electrophoresis sodium dodecyl sulfate (CE-SDS) (40° C., 4 weeks). In particular, % Main was measured as follows: A sample was prepared by mixing an SDS sample buffer (AB Sciex) and BME (2-mercaptoethaol, Sigma Aldrich) at a mixing ratio of about 1:50 (v:v). The sample was heat-treated at 70° C., and a % total protein area detected under 220 nm was analyzed using a CE analysis instrument (Beckman Coulter, PA800 plus) and a 32 karat software (Beckman Coulter). The measured % Mains (initial % Main, % Main at 4$^{th}$ wk, and Δ% Main (% Main at 4$^{th}$ wk—initial % Main)) are shown in Table 5 and FIGS. 3A and 3B:

TABLE 5

| Formulation | Initial % Main 1 | Initial % Main 2 | 40° C./4 Wk % Main 1 | 40° C./4 Wk % Main 2 | 40° C./4 Wk Δ % Main 1 | 40° C./4 Wk Δ % Main 2 |
|---|---|---|---|---|---|---|
| Formulation 1 | 33.9 | 61.5 | 33.2 | 60.0 | −0.7 | −1.5 |
| Formulation 2 | 34.1 | 62.0 | 32.5 | 60.9 | −1.6 | −1.1 |
| Formulation 3 | 32.9 [SD: 2.12] | 61.6 [SD: 1.38] | 31.5 [SD: 1.97] | 59.3 [SD: 1.29] | −1.4 [SD:0.15] | −2.3 [SD:0.10] |
| Formulation 4 | 32.7 [SD: 2.00] | 61.6 [SD: 1.38] | 31.3 [SD: 2.06] | 59.7 [SD: 1.22] | −1.3 [SD: 0.06] | −1.9 [SD: 0.21] |
| EYLEA ® | 37.1 [SD: 0.12] | 55.7 [SD: 0.15] | 35.2 [SD: 0.00] | 54.4 [SD: 0.15] | −1.9 [SD: 0.12] | −1.3 [SD: 0.10] |

(Main1: N-glycan 4N form; Main 2: N-glycan 5N form) As shown in Table 5 and FIGS. 3A and 3B, the main amount (%) reduction rates of Formulations 1 and 2 not including a buffer under the conditions of a protein drug concentration of 40 mg/ml and pH 6.2 were low as compared with those of Formulations 3 and 4 including a buffer, and had no significant difference as compared with that of the control formulation, EYLEA®, which is a commercial formulation.

Example 5. Measurement of VEGF Binding Efficiency of Aflibercept

To test whether activity of aflibercept, which is a pharmacologically active ingredient in the formulation prepared in Example 1, was maintained or not, relative potency activity (% RPA) of aflibercept in the formulation with respect to VEGF was measured while storing the formulation under the conditions of a protein drug concentration of 40 mg/ml, pH 6.2, and a temperature of 40° C. for 4 weeks.

% RPA was measured as follows: in a 96-well plate sequentially loaded with aflibercept and VEGF, KDR 293 cells (Promega) were loaded and incubated, and then relative potency activity (% RPA) was analyzed using an envision microplate reader (Perkin Elmer, Envision 2014).

Figure 4:
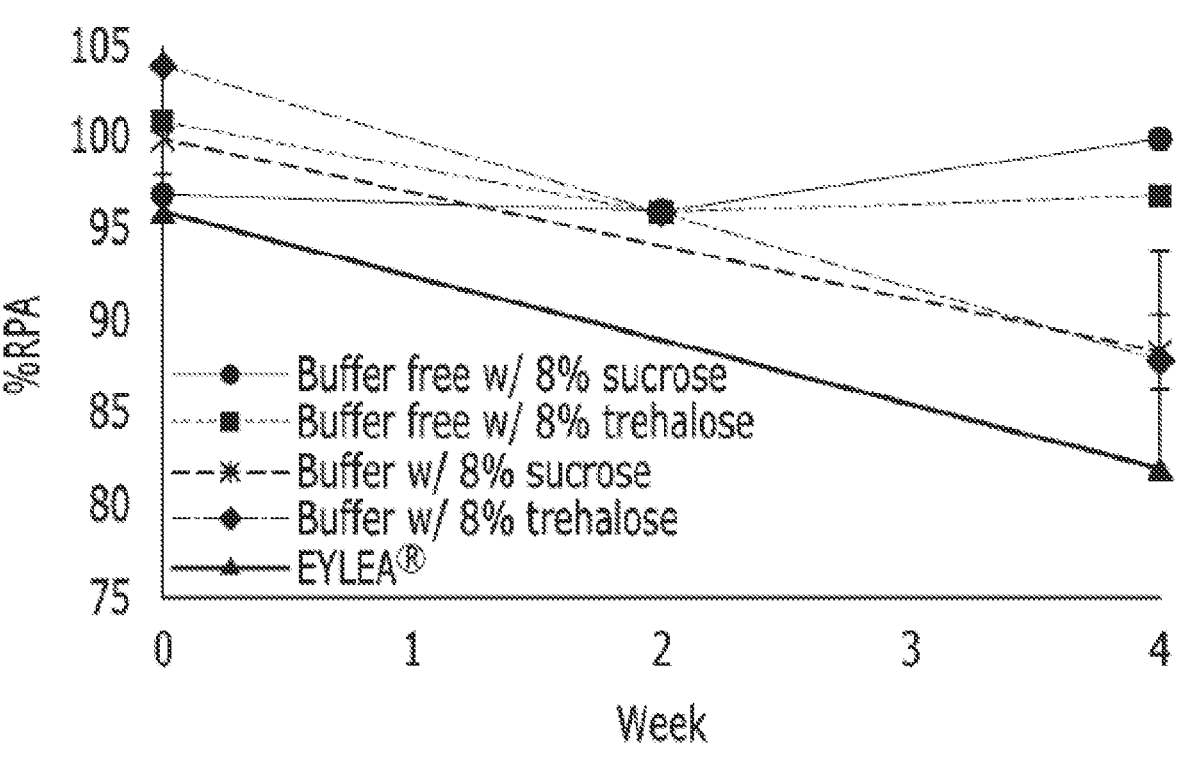
FIG. 4 is a graph showing a relative potency activity (% RPA) change rate (Δ% RPA) of a test formulation measured in Example 5 for 4 weeks after storing the test formulation at a temperature of 40° C. for 4 weeks.

The % RPA at 0th week (initial), % RPA at 4$^{th}$ week, and a % RPA change rate for 4 weeks (Δ% RPA) measured at 40° C. are shown in Table 6 and FIG. 4:

TABLE 6

| Candidate | Initial % RPA | 40° C./4 Wk % RPA | 40° C./4 Wk Δ % RPA |
|---|---|---|---|
| Formulation 1 | 97 | 100 | 3 |
| Formulation 2 | 101 | 96 | −5 |
| Formulation 3 | 100 [SD: 4] | 88 [SD: 2] | −12 [SD: 5] |
| Formulation 4 | 104 [SD: 6] | 88 [SD: 6] | −16 [SD: 6] |
| EYLEA ® | 96 | 82 | −14 |

As shown in Table 6 and FIG. 4, it was confirmed that potency (%) change rates of Formulations 1 and 2 not including a buffer under the conditions of a protein drug concentration of 40 mg/ml and pH 6.2 were excellent as compared with those of Formulations 3 and 4 including a buffer and the control formulation, EYLEA®, which is a commercial formulation.

Example 6. Measurement of HMW (%)
(Freeze/Thaw or Agitation Stress Condition)

To test stability of the liquid formulation prepared in Example 1 under various conditions, HMW (%) (% HMW; % high molecular weight; by weight) indicating a degree of aggregation of a protein drug in the formulation was measured using SE-HPLC under the conditions of a protein concentration of 40 mg/ml, pH 6.2, and freeze/thaw (5 cycles, where in each cycle: freezing for at least 18 hours at −70° C.+thawing for 1 to 2 hours at room temperature (25° C.) or agitation stress (at 400 rpm for 72 hours).

The measurement of HMW (%) was performed in the same manner described in Example 2.

Figure 5:
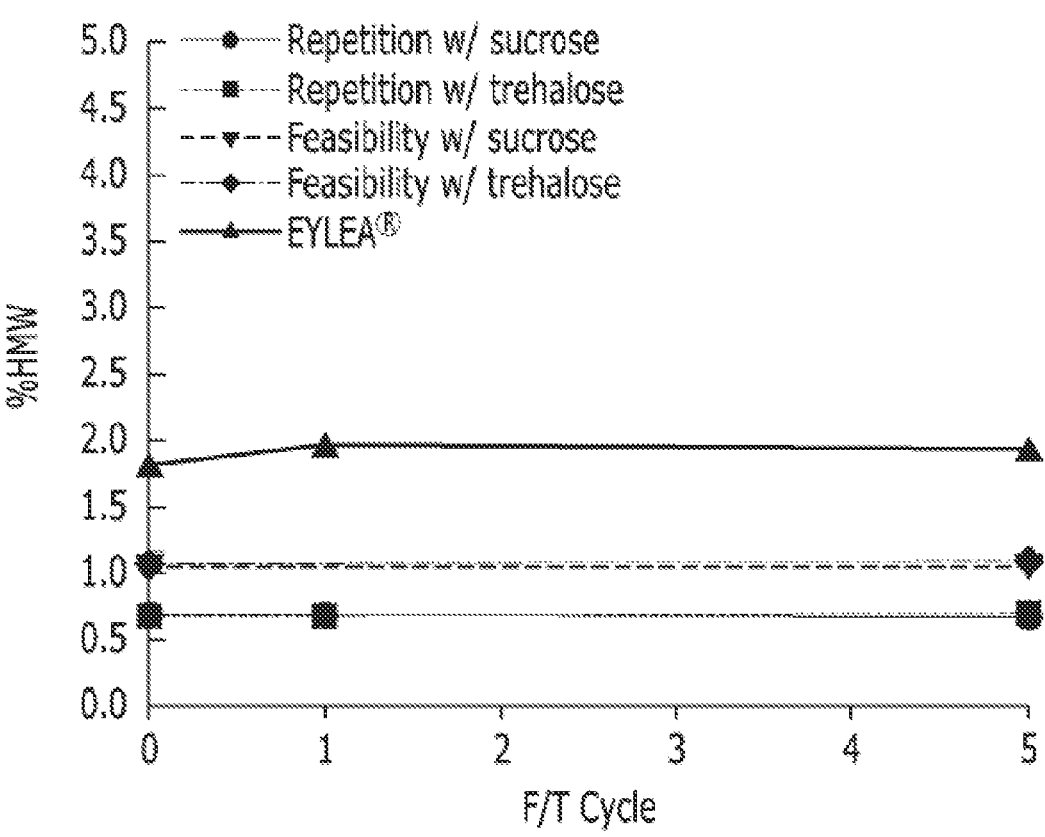
FIG. 5 is a graph showing a high-molecular weight % (% HMW) change rate (Δ% HMW) of a test formulation measured in Example 6 under freeze/thaw (5 cycles) conditions.

The % HMW of each of the formulations measured under the freeze/thaw (5 cycles) condition is shown in Table 7 and FIG. 5:

TABLE 7

| | Initial | Freeze/thaw (5 Cycles) | | |
|---|---|---|---|---|
| Candidate | % HMW | % HMW | Δ % HMW | |
| Formulation 1 (n = 3) | 0.67 | 0.69 | 0.02 | |
| | [SD: 0.01] | [SD: 0.01] | [SD: 0.00] | |
| Formulation 2 (n = 3) | 0.67 | 0.69 | 0.02 | |
| | [SD: 0.01] | [SD: 0.01] | [SD: 0.00] | |
| Formulation 3 (n = 3) | 0.81 | 0.97 | 0.17 | |
| | [SD: 0.09] | [SD: 0.09] | [SD: 0.03] | |
| Formulation 4 (n = 3) | 0.84 | 0.99 | 0.15 | |
| | [SD: 0.07] | [SD: 0.08] | [SD: 0.03] | |
| EYLEA ® (n = 3) | 1.81 | 1.95 | 0.15 | |
| | [SD: 0.03] | [SD: 0.01] | [SD: 0.02] | |

As shown in Table 7 and FIG. 5, degrees of increase in HMW (%) based on SE-HPLC analysis of Formulations 1 and 2 not including a buffer when exposed to the freeze/thaw conditions under the conditions of a protein drug concentration of 40 mg/ml and pH 6.2 were lower than those of Formulations 3 and 4 including a buffer and that of the control formulation, EYLEA®. Also, the % HMWs of Formulations 1 to 4 measured under the agitation stress condition is shown in Table 8 and FIG. 6:

TABLE 8

| | Control (No agitation, RT) | Agitation (400 rpm, 72 hours) | | |
|---|---|---|---|---|
| Candidate | % HMW | % HMW | Δ % HMW | |
| Formulation 1 (n = 3) | 0.81 | 0.84 | 0.03 | |
| | [SD: 0.00] | [SD: 0.00] | [SD: 0.00] | |
| Formulation 2 (n = 3) | 0.81 | 0.86 | 0.06 | |
| | [SD: 0.02] | [SD: 0.03] | [SD: 0.03] | |
| Formulation 3 (n = 3) | 1.00 | 1.03 | 0.04 | |
| | [SD: 0.05] | [SD: 0.08] | [SD: 0.03] | |
| Formulation 4 (n = 3) | 1.03 | 1.11 | 0.08 | |
| | [SD: 0.06] | [SD: 0.08] | [SD: 0.07] | |
| EYLEA ® (n = 3) | 1.96 | 1.95 | −0.01 | |
| | [SD: 0.01] | [SD: 0.01] | [SD: 0.02] | |

Figure 6:
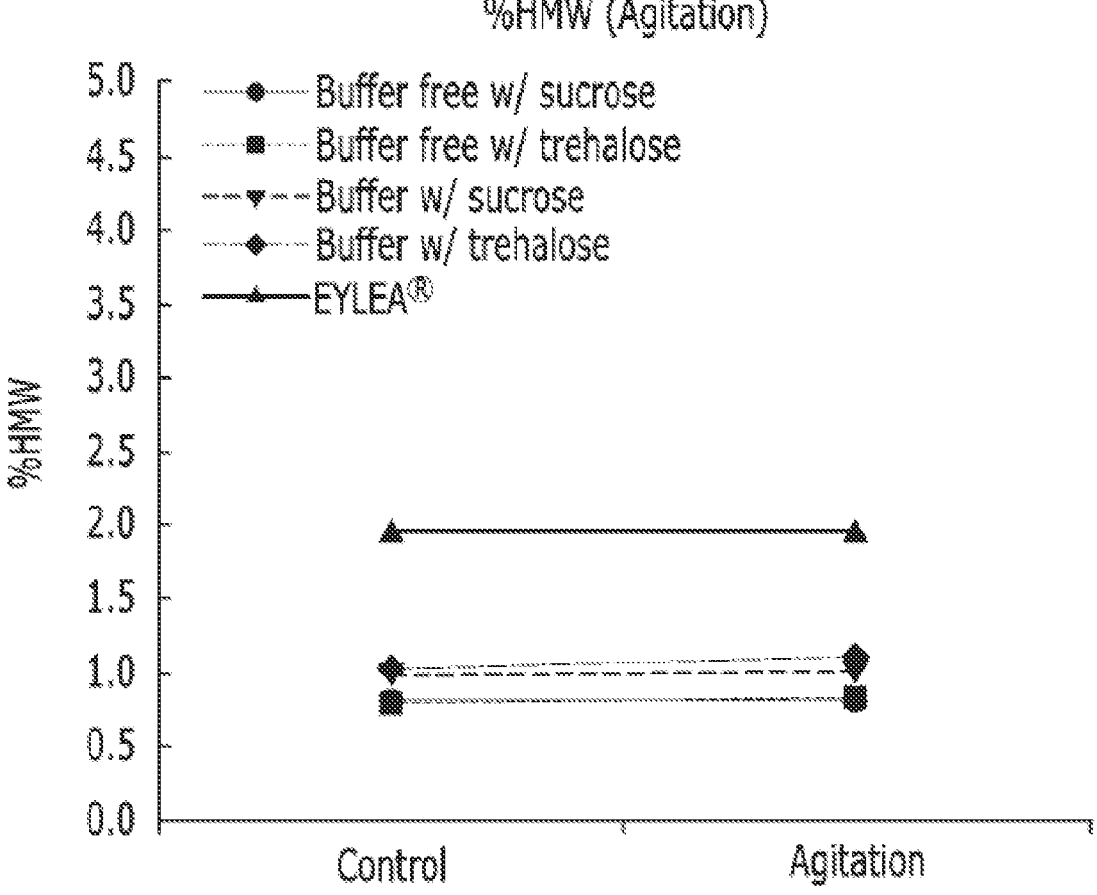
FIG. 6 is a graph showing high-molecular weight % (% HMW) change rate (Δ% HMW) of the test formulation measured in Example 6 under Agitation Stress (400 rpm and 72 hours) conditions.

As shown in Table 8 and FIG. 6, Formulations 1 and 2 not including a buffer had no significant increase in HMW amount (%) based on SE-HPLC analysis when exposed to agitation stress under the conditions of a protein drug concentration of 40 mg/ml and pH 6.2 as compared with those of Formulations 3 and 4 including a buffer and the control formulation, EYLEA®.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52 (e).

What is claimed is:

1. A liquid composition comprising:
(1) 5 mg/ml to 300 mg/ml of aflibercept;
(2) a stabilizer comprising a sugar; and
(3) a surfactant,
wherein the pH of the liquid composition is in a range of 4 to 8, and
wherein the liquid composition does not comprise any of the buffers selected from the group consisting of phosphoric acid, acetic acid, citric acid, succinic acid, carbonic acid, histidine, aspartic acid, and glutamic acid, or a pharmaceutically acceptable salt of the buffer.

2. The liquid composition of claim 1, wherein the sugar comprises at least one selected from the group consisting of trehalose, sucrose, and glucose.

3. The liquid composition of claim 1, wherein the stabilizer comprises at least one selected from the group consisting of 1 to 20% (w/v) of trehalose, and 1 to 20% (w/v) of sucrose.

4. The liquid composition of claim 1, wherein the stabilizer does not comprise sodium chloride.

5. The liquid composition of claim 1, wherein the surfactant is a non-ionic surfactant.

6. The liquid composition of claim 1, wherein the surfactant is comprised in an amount of 0.001 to 3% (w/v) based on the total amount of the composition.

7. The liquid composition of claim 1, wherein the liquid composition is isotonic.

8. The liquid composition of claim 1, wherein the liquid composition is for intravitreal administration.

9. The liquid composition of claim 8, wherein the stabilizer does not comprise sodium chloride.

10. An injection for intravitreal administration, the injection comprising the liquid composition of claim 1.

11. A liquid composition comprising:

(1) aflibercept;

(2) a stabilizer comprising a sugar; and (3) a surfactant, wherein the pH of the liquid composition is in a range of 5.7 to 6.7, and wherein the liquid composition does not comprise any of the buffers selected from the group consisting of phosphoric acid, acetic acid, citric acid, succinic acid, carbonic acid, histidine, aspartic acid, and glutamic acid, or a pharmaceutically acceptable salt of the buffer.

12. The liquid composition of claim 11, wherein the liquid composition is for intravitreal administration.

* * * * *